United States Patent
Otto et al.

(10) Patent No.: US 6,750,332 B1
(45) Date of Patent: Jun. 15, 2004

(54) SALICYL ALCOHOL DERIVATIVES

(75) Inventors: Ralf Otto, Bad Friedrichshall (DE); Albrecht Weiss, Langenfeld (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/856,835

(22) PCT Filed: Apr. 26, 2000

(86) PCT No.: PCT/EP00/03758

§ 371 (c)(1),
(2), (4) Date: Feb. 26, 2002

(87) PCT Pub. No.: WO00/68239

PCT Pub. Date: Nov. 16, 2000

(30) Foreign Application Priority Data

May 5, 1999 (DE) ......................................... 199 20 558
May 28, 1999 (DE) ......................................... 199 24 688

(51) Int. Cl.$^7$ ............................................. C07H 15/00
(52) U.S. Cl. ..................................... 536/4.1; 536/123.1
(58) Field of Search ................................ 536/4.1, 123.1

(56) References Cited

U.S. PATENT DOCUMENTS 5,876,737 A    3/1999   Schonrock et al. ......... 424/401

FOREIGN PATENT DOCUMENTS

| DE | 34 09 275   | 9/1985  |
| DE | 196 15 577  | 10/1997 |
| DE | 197 53 789  | 6/1999  |

OTHER PUBLICATIONS

Phytochemistry, 1992, 31(8), 2909–10 (Abstract only).*
Keapigu et al. (Zhongguo Yaoke Daxue Xuebao (1996), 27(5), 271–273) (abstract sent).*
Riva et al., "Protease–Catalyzed Regioselective Esterification of Sugars and Related Compounds in Anhydrous Dimethylformamide," J. Am. Chem. Soc., vol. 110, pp. 584–589, American Chemical Society, 1988.
Pearl, Irwin A. et al. Mass Spectrometry as an Aid for Determining Structures of Natural Glucosides, Phytochemistry, vol. 7, pp. 831–837, England, 1968.
Estes, Timothy, K. et al., Studies of the Bark of the Family Salicaceae, "Hot–water Extractive of the Green Bark of Populus Trichocarpa," TAPPI, vol. 50, No. 7, pp. 318–324, 1967.
Itoh, Atsuko et al., "Two New Phenolic Glycosides from *Alangium chinense*," Nat. Med., vol. 52, No. 2, pp. 173–175, Tokyo, 1997.
Otto et al., "Lipase–Catalyzed Synthesis of Arylaliphatic Esters of Beta–d(+)–Glucose, n–Alkyl– and Aryglucosides and Characterization of their Surfactant Properties," Journal of Biotechnology, Elsevier Science Publishers, vol. 64, No. 2–3, pp. 231–237, Amsterdam, (Oct. 8, 1998).
Otto et al., "Substrate Specifity of Lipase B from *Candida Antartica* in the Synthesis of Arylaliphatic Glycolipids," Journal of Molecular Catalysis B: Enzymatic, vol. 8, pp. 201–211, 2000.
Matsumura et al., Surface Activities, Biodegradability and Antimicrobial Properties of n–Alkyl Glucosides, Mannosides and Galactosides, J. Am. OilChem. Soc., vol. 67, No. 12, pp. 996–1001, 1990.
T. Hedner and B. Everts, "The Early Clinical History of Salicylates in Rheumatology and Pain", Clin. Rheumatol., vol. 12, pp. 17–25, 1998.
J.R. Vane, Inhibition of Prostaglandin Synthesis as a Mechanism of Action of the Aspirin–Like Drugs, Nature, pp. 231–235, 1971.
G. Fürstenberger, "Role of Eisosanoids in Mammalian Skin Epidermis", Cell. Biol. Rev., vol. 24, pp. 1–90, 1990.
G. Fürstenberger et al., "Partial Inversion of the Initiation–Promotion Sequence of Multistage Tumorigenesis in the Skin of NMRI Mice," Science, vol. 230, pp. 76–78, 1985.
L. van Hoof et al., Plant Viral Agents, VI. Isolation of Antiviral Phenolic Glucosides from *Populus cultivar Beaupre* by Droplet Counter–Current Chromatography, J. Nat. Prod., vol. 52, pp. 875–878, (1989).
C. Ferri, "Reaktionen der Organischen Synthese", Thieme–Verlag, Stuttgart, 1978 (not enclosed reciting entire book).
Ushiyama et al., "Biotransformation of Phenylcarboxylic Acids by Plant Cell Cultures," Phytochemistry, vol. 28, No. 12, pp. 3335–3339, 1989.
K. Drauz and H. Waldman, "Enzyme Catalysis in Organic Synthesis", VCH–Verlag, Weinheim, 1975 (not enclosed reciting entire book).

* cited by examiner

Primary Examiner—Samuel Barts
Assistant Examiner—Michael C. Henry
(74) Attorney, Agent, or Firm—John E. Drach; Aaron R. Ettelman

(57) ABSTRACT

Novel salicyl alcohol derivatives having valuable cosmetically and pharmaceutically useful properties, such as prostaglandin synthesis inhibition, corresponding to the formula (I):

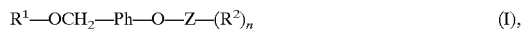

a method for producing the same and their utilization in cosmetics and pharmacy.

12 Claims, 2 Drawing Sheets

SALICYL ALCOHOL DERIVATIVES

CROSS-REFERENCE TO RELATED APPLICATIONS

This application is a U.S. National Stage application filed under 35 U.S.C. § 371, claiming priority under 35 U.S.C. §§ 119 and 365 of International Application No. PCT/EP00/03758, filed Apr. 26, 2000, in the European Patent Office and DE 199 20 558.2 and DE 199 24 688.2, filed respectively on May 5 and May 28, 1999, in the German Patent Office.

This invention relates to new salicyl alcohol derivatives, to processes for their preparation and to cosmetic and/or pharmaceutical preparations containing these compounds.

Many naturally occurring alkyl and phenol glucosides show antiviral, antimicrobial and, in some cases, anti-inflammatory effects (S. Matsamura, K. Imai, K. Kawada and T. Uchibori, Surface activities, biodegradability and antimicrobial properties of n-alkyl-glucosides, mannosides and galactosides, J. Am. Oil Chem. Soc. 67, 996–1001 (1990); T. Hedner and B. Everts, The early clinical history of salicylates in rheumatology and pain, Clin. Rheumatol. 12, 17–25 (1998)). Above all, aqueous extracts of willow bark (*Salix alba, purpurea* or *fragilis*) and poplar are known to have anti-inflammatory activity. Accordingly, corresponding extracts are used in medicinal teas and in cosmetic products, for example to reduce irritation of the skin, as described in German patent application DE 196 15 577. Important ingredients of willow bark include salicin and salicylic acid (o-hydroxybenzoic acid), salicortin (2-[[[(1-hydroxy-6-oxo-2-cyclohexen-1-yl)-carbonyl]oxy]methyl] phenyl-β-D-glucopyranoside) and fragilin (acetyl salicin) while the bark of poplars contains populin (benzoyl salicin). In the main, salicylic acid and its derivatives, such as acetyl salicylic acid, have been very thoroughly investigated for anti-inflammatory activity. As non-steroidal anti-inflammatory drugs (NSAID), they inhibit prostaglandin synthesis (J. R. Vane, Inhibition of prostaglandin synthesis as a mechanism of action of the aspirin-like drugs, Nature, 231, 232–235 (1971)).

Prostaglandins are formed as a reaction to various exogenous cell-specific stimuli by deoxygenation of polyunsaturated fatty acids, more particularly arachidonic acid, catalyzed by the enzymes prostaglandin-synthase-1 and -2 (PGHS-1 and -2). As autocrinal and paracrinal tissue hormones, they are formed to a greater extent in cases of injury or skin irritation, in wound healing processes and in inflammatory reactions.

Normal epidermis already contains significant quantities of prostaglandins which are evidently formed by PGHS-1 because PGHS-2 is not expressed. In irritated skin, prostaglandins (above all $PGE_2$ and $PGF_{27}$ from the keratinocytes) as local inflammation mediators promote both the dilation (widening) and also greater permeability of blood vessels and are thus involved in the reddening, heating and swelling of the skin typical of inflammation reactions (G. F ürstenberger, Role of eisosanoids in mammalian skin epidermis, Cell. Biol. Rev. 24, 1–90 (1990); G. F ürstenberger, V. Kinzel, M. Schwarz and F. Marks, Partial inversion of the initiation-promotion sequence of multistage tumorigenesis in the skin of NMRI mice; Science 230, 76–78 (1985)) and in the development of a regenerative epidermal hyperplasia. Prostaglandin synthesis inhibitors are capable of preventing these unwanted effects.

Besides the salicin derivatives occurring in willow and poplar mentioned at the beginning, the isolation of benzoyl salicin from plants is known from the literature (L. van Hoof et al., Plant viral agents, VI. Isolation of antiviral phenolic glucosides from Populus cultivar Beaupre by droplet counter-current chromatography, J. Nat. Prod. 52, 875–878 (1989)) as is the enzymatic production of phenyl butyryl salicin (R. T. Otto, U. T. Bornscheuer, C. Syldatk and R. D. Schmid, Lipase-catalyzed synthesis of arylaliphatic esters of D(+)-glucose, alkyl- and aryl-glucosides and characterization of their surfactant propeties; J. Biotechnol. 64, 231–237 (1998)).

Figure 1:
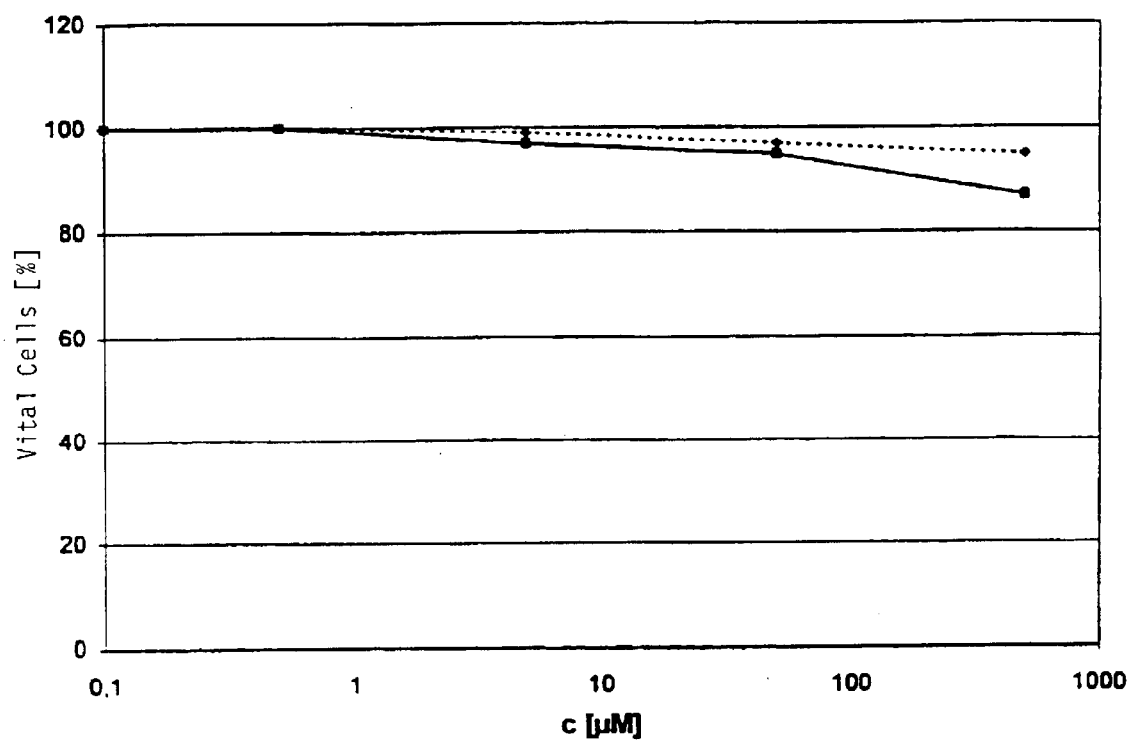
FIG. 1 plots the influence of phenylpropionyl salicin (lower solid-line curve) and p-OH-phenylacetyl salicin (upper dotted-line curve) on the vitality of skin cells (keratinocytes).

DESCRIPTION OF THE INVENTION.

Although numerous pharmacologically active substances intervening, for example, in the inflammation cascade are already known in the literature, there is still a need for more effective active principles with minimal side effects. There is also a need for active principles which are readily absorbed by and rapidly penetrate into the skin and which, in addition, must readily lend themselves to incorporation in pharmaceutical or cosmetic formulations.

It has now surprisingly been found that certain salicyl alcohol derivatives, which may be regarded from their chemical structure as related to salicin, show cosmetically and pharmaceutically useful pharmacological effects such as, for example, anti-inflammatory, antipyretic, antiphlogistic and/or analgesic effects and have fewer, if any, of the above-described disadvantages of the prior art.

The present invention relates to salicyl alcohol derivatives corresponding to general formula (I):

$$R^1\text{—}OCH_2\text{—}Ph\text{—}O\text{—}Z\text{—}(R^2)_n \quad\quad (I),$$

to processes for their production and to cosmetic or pharmaceutical preparations containing these compounds. The compounds show valuable pharmacological properties such as, for example, an inhibiting effect on prostaglandin synthesis. In general formula (I):

$R^1$ is a hydrogen atom or a $C(O)R^3$ group where $R^3$ is an alkyl, cycloalkyl, cycloalkylalkyl, aralkyl or aryl group containing 1 to 26 carbon atoms and/or 1–10 hetero atoms which may be unbranched or branched, mono- or polyunsaturated and/or may bear substituents on the carbon chain and/or at the hetero atoms, Ph is the 1,2-phenylene group, Z is a sugar hemiacetally attached to the aromatic group Ph in (I) and optionally substituted n-times by $R^2$ like an ester; the sugar may be a mono-, di-, oligo- or polysaccharide, n is an integer between 0 and m, m being equal to the number of free hydroxyl groups present in the sugar Z hemiacetally attached to the aromatic group, $R^2$ is a hydrogen atom or a group $C(O)R^4$ where $R^4$ is selected from the same group as $R^3$; $R^1$ and $R^2$ may be the same or different with the proviso that at most one of the two substituents $R^1$ or $R^2$ is hydrogen when Z is glucose, and on the conditions that where Z is glucose and $R^2$ is hydrogen, $R^1$ cannot be acetyl or benzoyl or (1-hydroxy-6-oxo-2-cyclohexen-1-yl)

carbonyl and, where $R^1$ is hydrogen, Z is glucose and n=1 and the glucose unit is substituted by $R^2$ at its primary hydroxy group, $R^2$ cannot be 4-phenylbutyryl. Where $R^1$ is hydrogen, Z is glucose and n=1 and the glucose unit is substituted by $R^2$ at its primary hydroxy group, the carboxylic acid $R^4$COOH corresponding to the substituent $R^2$ is preferably not a hydrophobic aromatic carboxylic acid.

The meanings mentioned at the beginning in the definition of the substituents include, for example, for $R^3$ and $R^4$: hydrogen, the methyl, ethyl, propyl, n-butyl, tert.butyl, pentyl, hexyl, heptyl, octyl, nonyl, decyl, undecyl, dodecyl, tridecyl, tetradecyl, pentadecyl, hexadecyl, heptadecyl, octadecyl, heneicosyl, vinyl, 1-propenyl, 2-propenyl, 2-butenyl, 8-pentadecenyl, 8-heptadecenyl, Z,Z-8,11-heptadecadienyl, Z,Z,Z-8,11,14-heptadecatrienyl, 4,7,10,13,16-nonadecapentaenyl, 3,6,9,12,15,18-heneicosahexaenyl, phenyl, phenyl methyl, phenylethyl, phenylpropyl, phenylbutyl, o-, m- or p-hydroxyphenyl, o-, m- or p-hydroxyphenylmethyl, o-, m- or p-hydroxyphenylethyl, o-, m- or p-hydroxyphenylpropyl, o-, m- or p-hydroxyphenylbutyl, 3,4,5-trihydroxyphenyl, 3-phenylvinyl, o-, m- or p-hydroxy-3-phenylvinyl, 3-(3,4-dihydroxyphenyl)-vinyl or 3-pyridyl group, additional substituents such as, for example, a halogen atom, an alkyl, hydroxy, alkoxy, phenyl, nitro, amino, acetylamino or carboxy group optionally being present, and phenolic hydroxy groups optionally being present as phenolate salts with alkali metal or alkaline earth metals.

Accordingly, the present invention also relates to salicyl alcohol derivatives corresponding to general formula (I) in which at least one of the two substituents $R^1$ and $R^2$ is a hydrogen atom, the benzoyl, phenylacetyl, phenylpropionyl, phenylbutyryl, phenylvaleroyl, o-, m- or p-hydroxybenzoyl, o-, m- or p-hydroxyphenylacetyl, o-, m- or p-hydroxyphenylpropionyl, o-, m- or p-hydroxyphenylbutyryl, o-, m- or p-hydroxyphenylvaleroyl, 3,4,5-trihydroxybenzoyl, 3-phenylacryloyl, o-, m- or p-hydroxy-3-phenylacryloyl or 3-(3,4-dihydroxyphenyl)-acryloyl group.

Preferred salicyl alcohol derivatives corresponding to general formula (I) are those in which n=1 and $R^1$ is hydrogen.

The substituent Z in general formula (I) may be selected, for example, from threose, erythrose, arabinose, lyxose, ribose, xylose, allose, altrose, galactose, glucose, gulose, idose, mannose, talose, fructose, the naturally occurring stereoisomers of the sugars being preferred, and the di-, oligo- and polysaccharides consisting of these sugars.

Preferred salicyl alcohol derivatives corresponding to general formula (I) are those in which Z stands for D-glucose.

In principle, the compounds according to the invention may be prepared, for example, by any of the processes described in the literature for the production of carboxylic acid esters (cf. C. Ferri, Reaktionen der organischen Synthese, Thieme-Verlag, Stuttgart 1978) although they are preferably prepared by esterifications, transesterifications and acylations with activated carboxylic acid derivatives.

Accordingly, the present invention also relates to a process for the production of the compounds (I) according to the invention which is characterized in that an alcohol component is esterified or transesterified with a carboxylic acid, a carboxylic acid ester or an activated carboxylic acid derivative in the presence of suitable catalysts.

An activated carboxylic acid derivative in the context of the invention is understood to be, for example, a carboxylic acid chloride or carboxylic anhydride which may be reacted with an alcohol component under Schotten-Baumann conditions to form an ester.

The compounds according to the invention may be prepared, for example, by esterification of an alcohol corresponding to formula (II)

$$HOCH_2—Ph—O—Z \qquad (II)$$

with a carboxylic acid $R^3$COOH and/or $R^4$COOH in which Ph, Z, $R^3$ and $R^4$ are as defined for formula (I); in the case of esterification with both carboxylic acids, the esterification may be carried out in a single step or even in two successive steps.

In addition, the compounds according to the invention may be prepared by transesterification of an alcohol corresponding to formula (II) with carboxylic acid esters $R^3$COOR$^5$ and/or $R^4$COOR$^5$ in which Ph, Z, $R^3$ and $R^4$ are as defined for formula (I) and $R^5$ is an alkyl group containing 1 to 4 carbon atoms; in the case of transesterification with both carboxylic acid esters, the transesterification may be carried out in a single step or even in two successive steps.

In the preparation of the compounds according to the invention by the standard methods of chemical synthesis, mixtures of mono- and poly-substituted products are generally formed on account of the presence of several free hydroxyl groups in the alcohol component (II) or a partial ester thereof, so that protective groups have to be introduced and removed if a particular compound is to be specifically synthesized.

The use of activated carboxylic acid derivatives results in the formation of by-products and, in many cases, also unwanted secondary products which complicate working up, reduce the yields of desired product and pollute the environment. These disadvantages can be avoided or at least reduced by carrying out the production of the compounds according to the invention enzymatically (for example by the process described in German patent application DE 197 53 789.8) or by biotransformations with plant cell cultures (M. Ushiyama, S. Kumagai and T. Furuya, Phytochemistry 28, 3335 (1989)).

Accordingly, the present invention also relates to a process for the production of the compounds (I) according to the invention which is characterized in that an alcohol component is esterified or transesterified with a carboxylic acid or a carboxylic acid ester in the presence of one or more enzymes as catalysts.

Suitable enzymatic esterification or transesterification processes are described, for example, in K. Drauz and H. Waldman, Enzyme Catalysis in Organic Synthesis, VCH-Verlag, Weinheim 1975.

The salicyl alcohol derivatives according to the invention have valuable biological activities such as, for example, anti-inflammatory, antipyretic, antiphlogistic or analgesic effects. Thus, prostaglandin synthesis is inhibited to a greater extent with the compounds according to the invention than, for example, with compounds known from the literature, such as salicin, which is associated with the greater lipophilia of the compounds according to the invention. The better effect is dependent inter alia on efficient absorption by the cell membranes of the keratinocytes. The lipid solubility of glycosidic compounds derives from the ratio of hydrophilic component to hydrophobic component which is described by the HLB value. Salicin which has an HLB value of about 12 is more of a water-soluble molecule whereas salicin esters with HLB values of, in some cases, well below 10 are more liposoluble molecules. As a result, transport through the cell membranes is distinctly improved in relation to salicin while cutaneous application is facilitated or actually made possible in relation to conventional active principles which, in general, only develop an adequate effect with subcutaneous application.

The carboxylic acid component of the salicyl alcohol derivatives according to the invention can be formed by a carboxylic acid $R^3COOH$ and/or $R^4COOH$ which itself has intrinsic biological activity such as, for example, sorbic acid, a known fungistatic agent. Salicyl alcohol derivatives which show other biological effects, for example antioxidative, skin-lightening, antibacterial, antiviral and fungistatic effects, besides anti-inflammatory, antipyretic, antiphlogistic and analgesic effects, can be obtained in this way.

In addition, the compounds according to the invention can be incorporated particularly well in lipophilic basic formulations and may readily be formulated as stable emulsions.

According to the invention, the compounds of general formula (1) are used for the production of cosmetic and/or pharmaceutical preparations.

Accordingly, the present invention also relates to cosmetic and/or pharmaceutical preparations containing the salicyl alcohol derivatives (I) according to the invention.

The cosmetic preparations obtainable using the compounds (I) in accordance with the invention, for example hair shampoos, hair lotions, foam baths, shower baths, creams, gels, lotions, alcoholic and aqueous/alcohol solutions, emulsions, wax/fat compounds, stick preparations, powders or emollients, may contain mild surfactants, oil components, emulsifiers, superfatting agents, pearlizing waxes, consistency factors, thickeners, polymers, silicone compounds, fats, waxes, stabilizers, biogenic agents, deodorizers, antidandruff agents, film formers, swelling agents, UV protection factors, antioxidants, hydrotropes, preservatives, insect repellents, self-tanning agents, solubilizers, perfume oils, dyes, germ inhibitors and the like as further auxiliaries and additives.

The quantity in which the compounds according to the invention are used in cosmetic preparations is normally in the range from 0.01 to 5% by weight and preferably in the range from 0.1 to 1% by weight, based on the preparations.

For the production of pharmaceutical or even cosmetic preparations, the compounds of general formula (I) according to the invention, optionally in combination with other active principles may be incorporated together with one or more typical inert carriers and/or diluents, for example corn starch, lactose, cane sugar, microcrystalline cellulose, magnesium stearate, polyvinyl pyrrolidone, citric acid, tartaric acid, water, water/ethanol, water/glycerol, water/sorbitol, water/polyethylene glycol, propylene glycol, carboxymethyl cellulose or fat-containing substances, such as hard fat or suitable mixtures thereof, in typical galenic preparations, such as tablets, dragées, capsules, powders, suspensions, drops, ampoules, sirups or suppositories.

The daily dose required to obtain a corresponding effect in pharmaceutical applications is preferably 0.1 to 10 mg/kg body weight and more preferably 0.5 to 2 mg/kg body weight.

EXAMPLES

Example 1
6-O-phenylpropionyl-[2-(hydroxymethyl)phenyl]-β-D-glucopyranoside 5 mmol D-(−)-salicin [2-hydroxymethyl)phenyl-β-D-glucopyranoside], 7.5 mmol phenylpropionic acid, 4 g molecular sieve, 4 ml t-butanol and 2.5 g immobilized lipase B from Candida antarctica were incubated for 34 hours at 60° C. in a rotating 50 ml round-bottom flask. The reaction was monitored by thin-layer chromatography (silica gel 60 plates with fluorescence indicator; mobile solvent: chloroform/methanol/water 65/15/2 v/v/v; visualization: UV detection and with acetic acid/sulfuric acid/anisaldehyde (100:2:1 v/v/v) immersion reagent). The product was extracted with 20 ml of dichloromethane and purified by column chromatography (silica gel F60; mobile solvent: ethyl acetate/methanol 10/1 v/v). After purification, the yield was 32% (white solid).

$^{13}$C-NMR (CD$_3$OD): δ (ppm)=30.9 (C-2), 38.7 (C-3), 61.6 (C-7*), 65.2 (C-6'), 72.2 (C-4'), 75.6 (C-2'), 76.1 (C-5'), 78.4 (C-3'), 103.7 (C-1'), 117.6 (C-6*), 124.5 (C-4*), 127.6 (C-7), 130.1–131.0 (C-3*, C-5*, C-5, C-6, C-8, C-9), 132.8 (C-2*), 143.4 (C-4), 157.5 (C-1'), 175.2 (C'=O).

Example 2
6-O-p-OH-phenylacetyl-([2-hydroxymethyl)phenyl]-β-D-glucopyranoside 5 mmol D-(−)-salicin [2-hydroxymethyl)phenyl-δ-D-glucopyranoside], 7.5 mmol p-OH-phenylacetic acid, 4 g molecular sieve, 4 ml t-butanol and 2.5 g immobilized lipase B from Candida antarctica were incubated for 34 hours at 60° C. in a rotating 50 ml round-bottom flask. The reaction was monitored by thin-layer chromatography (silica gel 60 plates with fluorescence indicator; mobile solvent: chloroform/methanol/water 65/15/2 v/v/v; visualization: UV detection and with acetic acid/sulfuric acid/anisaldehyde (100:2:1 v/v/v) immersion reagent). The product was extracted with 20 ml of dichloromethane and purified by column chromatography (silica gel F60; mobile solvent: ethyl acetate/methanol 10/1 v/v). After purification, the yield was 17% (white solid).

$^{13}$C-NMR (CD$_3$OD): δ (ppm)=41.8 (C-2), 61.0 (C-7*), 65.0 (C-6'), 71.5 (C-4'), 74.9 (C-2'), 75.4 (C-5'), 77.8 (C-3'), 103.2 (C-1'), 117.1 (C-6*), 123.9 (C-4*), 129.4–132.3 (C-2*, C-3*, C-5*; C-4, C-5, C-7, C-8), 136.1 (C-3), 156.0–159.2 (C-1*, C-6), 173.31 (C=O).

The following compounds were obtained in the same way as described in Example 1:

Example 3
p-chlorophenylacetoyl-([2-(hydroxymethyl)phenyl]-β-D-glucopyranoside $^{13}$C-NMR (CD$_3$OD): δ (ppm)=41.2 (C-2), 61.0 (C-7*), 65.1 (C-6'), 71.4 (C-4'), 74.9 (C-2'), 75.2 (C-5'), 77.8 (C-3'), 103.1 (C-1'), 117.7 (C-6*), 123.9 (C-4*), 129.5–132.0 (C-3–C-5, C-7, C-8, C-2*, C-3*, C-5*), 134.2 (C-6), 156.2 (C-1'), 173.0 (C'=O).

Example 4
6-O-cinnamoyl-([2-(hydroxymethyl)phenyl]-β-D-glucopyranoside $^{13}$C-NMR (CD$_3$OD): δ (ppm)=61.0 (C-7*), 64.9 (C-6'), 71.8 (C-4'), 74.9 (C-2'), 75.4 (C-5'), 77.9 (C-3'), 103.7 (C-1'), 117.1 (C-6*), 118.6 (C-2), 123.8 (C-4*), 129.1–131.6 (C-5 bis C-9, C-2*, C-3*, C-5*), 135.6 (C-4), 146.5 (C-3), 156.2 (C-1*), 168.3 (C'=O).

Example 5
6-O-oleoyl-([2-(hydroxymethyl)phenyl]-β-D-glucopyranoside $^{13}$C-NMR (CD$_3$OD): δ (ppm)=14.4.(C-18), 23.6 (C-17), 23.7–35.1 (C-11 bis C-16, C-2 bis C-8), 60.9 (C-7*), 64.7 (C-6'), 71.7 (C-4'), 74.9 (C-2'), 75.3 (C-5'), 77.8 (C-3'), 103.6 (C-1'), 117.1 (C-6*), 123.1 (C-4*), 129.0–132.8 (C-9, C-10, C-2*, C-3*, C-5*), 156.2 (C-1*), 175.5 (C'=O).

Example 6
6-O-palmitoyl-([2-(hydroxymethyl)phenyl]-β-D-glucopyranoside

In a two-necked flask surmounted by a Soxhlet extractor (filled with activated molecular sieve), 0.5 g of immobilized Candida antarctica B lipase (SP 435, manufacturer Novo Nordisk) was added to 5 mmol D-(−)-salicin ([2-(hydroxymethyl)phenyl]-β-D-glucopyranoside) and 5 mmol palmitic acid methyl ester in 50 ml acetone, followed by heating with stirring (magnetic stirrer, 200 r.p.m.) under reduced pressure for 48 h to 40° C. The progress of the reaction was followed by thin-layer chromatography. After the end of the reaction, 14 g warm acetone (ca. 50° C.) were added and the mixture was filtered at 50° C. The filtrate was cooled to −10° C. and the product precipitated was isolated in a yield of 53% by filtration.

$^{13}$C-NMR (CD$_3$OD): δ (ppm)=14.47 (C-16), 23.74 (C-15), 26.00 (C-3), 30.22–30.80 (C-4–C-13), 33.08 (C-14), 35.03 (C-2), 60.98 (C-7*), 64.59 (C-6'), 71.64 (C-4'), 74.96 (C-2'), 75.49 (C-5'), 77.82 (C-3'), 103.22 (C-1'), 117.07 (C-6*), 123.82 (C-4*), 129.78–132.34 (C-2*, C-3*, C-5*), 156.98 (C-1*), 175.23 (C=O). Anal. calculated for C$_{29}$H$_{48}$O$_8$ (524.69): C, 66.39; H, 9.22. Found: C, 67.88; H, 9.41.

Examples 7 to 9
Preparation of Other Salicin Esters by Transesterfication:

Salicin ([2-(hydroxymethyl)phenyl]-β-D-glucopyranoside) was reacted with various carboxylic acid methyl esters by the method described in Example 6 and the salicins selectively esterified at the primary alcohol function of the glucose unit listed in the following Table were obtained.

| Compound | Reaction temperature | Reaction time | Yield |
|---|---|---|---|
| Salicin stearate (Example 7) | 40° C. | 24 h | 67% |
| Salicin myristate (Example 8) | 35° C. | 48 h | 29% |
| Salicin phenyl acetate (Example 9) | 35° C. | 48 h | 32% |

The salicin esters thus prepared were characterized by NMR spectroscopy; the spectrum of Example 9 is shown by way of example below:
6-O-phenylacetyl-([2-(hydroxymethyl)phenyl]-β-D-glucopyranoside) (Example 9)

$^{13}$C-NMR (CD$_3$OD): δ (ppm)=41.82 (C-2), 60.99 (C-7*), 65.03 (C-6'), 71.52 (C-4'), 74.94 (C-2'), 75.49 (C-5'), 77.77 (C-3'), 103.21 (C-1'), 117.11 (C-6*), 123.91 (C-4*), 127.89 (C-6), 129.46–132.37 (C-2*, C-3*, C-5*; C-4, C-5, C-7, C-8), 136.12 (C-3), 156.95 (C-1*), 173.31 (C=O). Anal. calculated for C$_{21}$H$_{24}$O$_8$ (404.41): C, 62.38; H, 5.98. Found: C, 63.96; H, 5.90.

Example 10
Cytotoxicity (in Mouse or Human Skin Keratinocytes, MSCP 5 or HPK II)

The toxicity of the substances was investigated by the MTT Test (Mosmann 1983) in cell cultures. This test is based on the conversion of the yellow tetrazolium salt MTT into the violet dye formazane. The reaction takes place only in living cells through the succinate dehydrogenase located in the inner mitochondrial membranes. On account of the potential use in cosmetic or pharmaceutical products, skin cells (human HPKII or mouse MSCP 5 keratinocytes) were used as the test system. The substances tested (phenylpropionyl salicin and p-OH-phenyl acetyl salicin) were non-toxic to the cells in concentrations in which they showed biological activity (inhibition of prostaglandin synthesis). The effect of the substances on the keratinocytes was independent of the time (incubation time 1.5 or 20 h), the growth state (confluent or subconfluent) and the organism (mouse or human).

FIG. 1 shows that the influence of phenylpropionyl salicin (lower solid-line curve) and p-OH-phenylacetyl salicin (upper dotted-line curve) on the vitality of skin cells (keratinocytes) was minimal. The substances were dissolved in the culture medium and incubated with the cells for 20 h. The MTT reduction test was then carried out with fresh medium without test components.

Example 11
Inhibition of Prostaglandin Synthesis by Salicin Derivatives (in Mouse or Human Skin Keratinocytes MSCP 5 or HPK II)

Figure 2:
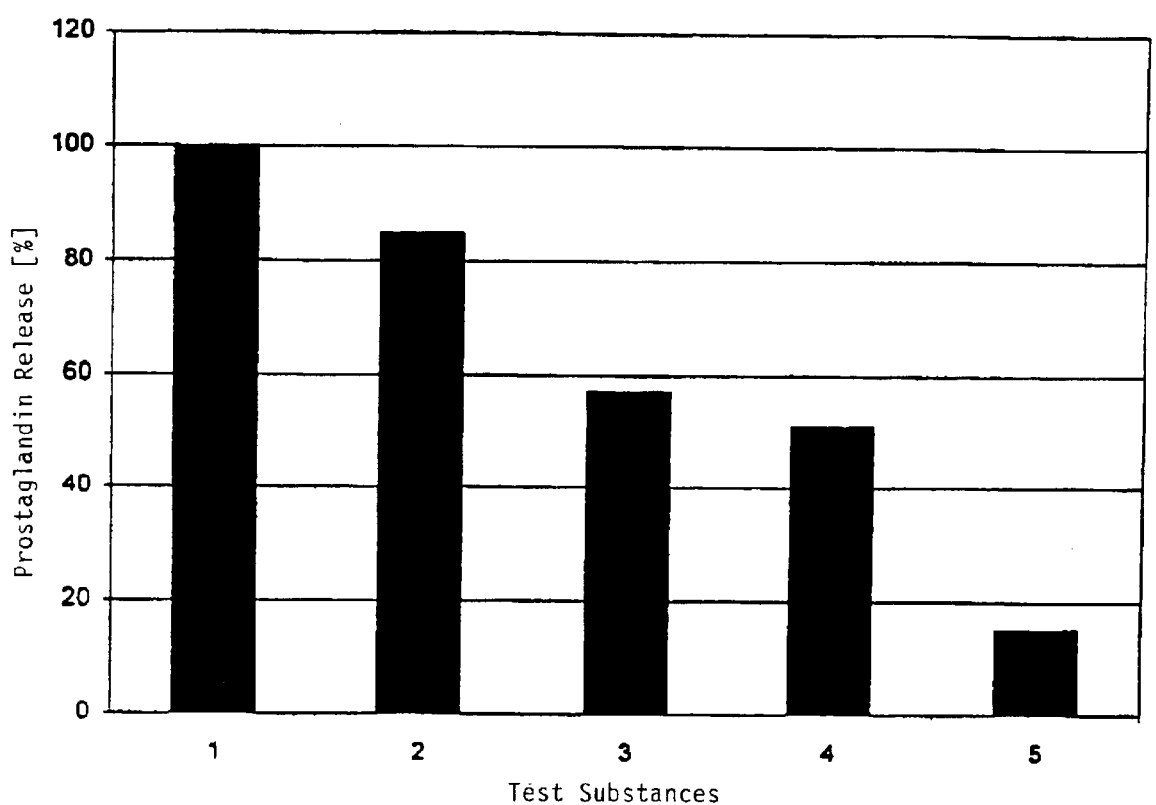
FIG. 2 shows the inhibiting effects of salicin and salicin esters on the release of prostaglandins in keratinocytes.

FIG. 2 shows the inhibiting effects of salicin and salicin esters on the release of prostaglandins in keratinocytes. The cells were marked for 16 hours with 0.2 μCi $^{14}$C-arachidonic acid ml$^{-1}$ medium. The test substances were added in fresh medium with increasing concentrations and incubated for 2 hours. In the Figure, the substances have the following meanings:

1=negative control
2=salicin
3=phenylpropionyl salicin
4=p-OH-phenyl acetyl salicin
5=positive control In the positive control NS398 (10 μm) for MSCP5 cells, prostaglandin synthesis is reduced by 85%. The prostaglandins were identified by comparison with reference substances and quantified by radiosensitometry. The result is expressed as the average value of three measurement points: MSCP 5: 100%=201 cpm; HPK II: 100%=63 cpm.

Example 12
Influencing of the Transcription Activity of HPK II (Human Skin Keratinocytes)

The release of prostaglandins can be influenced by inhibitors at several levels. Besides inhibition of the catalytic activity of the prostaglandin synthase proteins, another possible effect is on the messenger RNA of the cyclooxygenases. It was found in Northern Blot analyses that, when subconfluent MSCP 5 cells are incubated for 45 mins. with 500 μM p-OH-phenylacetoyl salicin, the COX-2-mRNA steady state concentration is greatly reduced by comparison with untreated cells. As a negative control, the cells were incubated for 45 minutes in medium containing only the solubilizer acetone (0.25%) but no test substance for the same recorded RNA concentration.

What is claimed is:
1. A salicyl alcohol derivative of the formula (I):

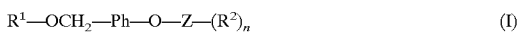

$$R^1—OCH_2—Ph—O—Z—(R^2)_n \qquad (I)$$

wherein R$^1$ represents a hydrogen atom or a C(O)R$^3$ group, wherein R$^3$ represents an alkyl, cycloalkyl, cycloalkylalkyl, aralkyl or aryl group having from 1 to 26 carbon atoms and/or from 1 to 10 heteroatoms, and wherein R$^3$ may be unbranched or branched, mono- or polyunsaturated and/or may bear substituents on the carbon chain and/or at the heteroatoms; Ph represents a 1,2-phenylene group, Z represents a sugar hemiacetally attached to the 1,2-phenylene group and substituted up to n-times by R$^2$, wherein the sugar may comprise a mono, di-, oligo- or polysaccharide; n is an integer between 0 and m, wherein m is equal to the number of free hydroxyl groups present in the sugar; wherein each R² independently represents a hydrogen atom or a C(O)R⁴ group wherein R⁴ is independently selected from the same group as R³; R¹ and R² may be the same or different; with the proviso that at most one of the two substituents R¹ or R² is hydrogen when Z is glucose; with the proviso that where Z is glucose and R² is hydrogen, R¹ is not an acetyl, a benzoyl or a (1-hydroxy-6-oxo-2-cyclohexen-1-yl)carbonyl; with the proviso that where R¹ is hydrogen, Z is glucose and n equals 1, the glucose unit is substituted by R² at its primary hydroxy group and R² is not 4-phenylbutyryl or a hydrophobic aromatic carboxylic acid moiety.

2. The salicyl alcohol derivative according to claim 1, wherein at least one of the two substituents R¹ and R² is a hydrogen atom, or a benzoyl, phenylacetyl, phenylpropionyl, phenylbutyryl, phenylvaleroyl, o, m- or p-hydroxybenzoyl, o-, m- or p-hydroxyphenylacetyl, o-, m- or p-hydroxyphenylpropionyl, o-, m- or p-hydroxyphenylbutyryl, o-, m- or p-hydroxyphenylvaleroyl, 3,4,5-trihydroxybenzoyl, 3-phenylacryloyl, o-, m- or p-hydroxy-3-phenylacryloyl or 3-(3,4-dihydroxyphenyl)-acryloyl group.

3. The salicyl alcohol derivative according to claim 1, wherein n equals 1 and R¹ is hydrogen.

4. The salicyl alcohol derivative according claim 2, wherein n equals 1 and R¹ is hydrogen.

5. The salicyl alcohol derivative according to claim 1, wherein Z is a monosaccharide selected from the group consisting of threose, erythrose, arabinose, lyxose, ribose, xylose, allose, altrose, galactose, glucose, gulose, idose, mannose, talose, and fructose.

6. The salicyl alcohol derivative according to claim 5, wherein Z is D-glucose.

7. The salicyl alcohol derivative according to claim 1, wherein R¹ is hydrogen, Z is glucose, and n equals 1.

8. A process for the production of the salicyl alcohol derivative of claim 1, the process comprising: esterifying or transesterifying with a carboxylic acid R³COOH and/or R⁴COOH, a carboxylic acid ester R³COOR⁵ and/or R⁴COOR⁵, or an activated carboxylic acid derivative, an alcohol of the formula (II), in the presence of a suitable catalyst:

wherein Ph, Z, R³, and R⁴ are as defined for formula (I), and R⁵ represents an alkyl group having from 1 to 4 carbon atoms.

9. The process according to claim 8, carried out by enzyme-catalyzed esterification or transesterification.

10. A method of preparing a cosmetic or pharmaceutical preparation, comprising: preparing the salicyl alcohol derivative according to claim 1, and combining the derivative with a cosmetically or pharmaceutically acceptable carrier.

11. A method of inhibiting prostaglandin synthesis, comprising: applying a prostaglandin synthesis inhibitive amount of a cosmetic or pharmaceutical preparation comprising the salicyl alcohol derivative according to claim 1 to a host in need of prostaglandin synthesis inhibition.

12. A cosmetic or pharmaceutical preparation, comprising the salicyl alcohol derivative according to claim 1 and a cosmetically or pharmaceutically acceptable carrier.

* * * * *